United States Patent [19]

Hall

[11] Patent Number: 4,955,379

[45] Date of Patent: Sep. 11, 1990

[54] MOTION ARTEFACT REJECTION SYSTEM FOR PULSE OXIMETERS

[75] Inventor: Peter R. Hall, Dyfed, United Kingdom

[73] Assignee: National Research Development Corporation, London, England

[21] Appl. No.: 229,692

[22] Filed: Aug. 8, 1988

[30] Foreign Application Priority Data

Aug. 14, 1987 [GB] United Kingdom ............... 8719333

[51] Int. Cl.⁵ ................................................ A61B 5/00
[52] U.S. Cl. ..................................... 128/633; 128/664; 128/666; 128/687
[58] Field of Search ............... 128/633, 634, 664, 665, 128/666, 687; 356/39, 41

[56] References Cited

U.S. PATENT DOCUMENTS

| | | | |
|---|---|---|---|
| 4,109,643 | 8/1978 | Bond et al. | 128/666 |
| 4,167,331 | 9/1979 | Nielsen | 356/41 |
| 4,260,951 | 4/1981 | Lewyn | 128/690 |
| 4,353,152 | 10/1982 | O'Connor et al. | 128/666 |
| 4,641,658 | 2/1987 | Lepper | 128/633 |
| 4,651,741 | 3/1987 | Passafaro | 128/633 |
| 4,723,554 | 2/1988 | Oman | 128/633 |

Primary Examiner—Kyle L. Howell
Assistant Examiner—John C. Hanley
Attorney, Agent, or Firm—Howard F. Mandelbaum

[57] ABSTRACT

A pulse oximeter apparatus characterized in that it comprises a bandpass filter adapted selectively to exclude motion artefact from wanted signal is disclosed.

Also disclosed is the use of such an apparatus for the determination of pulse rate and/or arterial blood oxygen saturation.

6 Claims, 4 Drawing Sheets

MOTION ARTEFACT REJECTION SYSTEM FOR PULSE OXIMETERS

BACKGROUND OF THE INVENTION

This invention relates to a motion artefact rejection system for pulse oximeters; more particularly, it relates to a system for filtering out signals due to patient movement, i.e. motion artefact signals, from wanted signals.

The operation of pulse oximeters which measure arterial blood oxygen saturation and pulse rate is prejudiced when the patient performs any movement. Oximeters have difficulty in distinguishing the pulsating signals due to arterial blood flow from the pulsating signals due to patient movement. Since the results are calculated from this pulsatile signal and the size thereof, it is highly desirable to be able to distinguish signals from these two sources. The present invention, which encompasses an apparatus and the use thereof, reduces the severity of this problem and offers significant advantages to a clinician.

In general terms, a pulse oximeter apparatus will typically comprise the following units: a sensor, containing two LEDs of different wavelength (commonly 660 nm and 940 nm), and a photodetector, which are applied directly to a patient. The sensor is connected to the main instrument by a cable. The instrument contains a system to adjust LED power, hence controlling light intensity, and a system to analyse the incoming light from the photodetector. Means are provided to isolate the pulsatile components of these incoming light signals. The nonvarying ("DC signals") at each wavelength are either maintained equal by the LED power adjusting system, whereby the effects thereof cancel, or they may themselves be isolated and measured. The time-varying signals ("AC signals") then pass through an AGC (automatic gain control) system to ensure that they supply an adequate signal to an analogue-to-digital converter, where they are digitised. The AC and DC signals are then taken into a microprocessor, which analyses the AC signals for amplitude and frequency (corresponding to pulse rate). Oxygen saturation is calculated by the microprocessor by inserting the amplitudes of the various signals into the following formula:

$$\frac{AC_1/DC_1}{AC_2/DC_2}$$

and reading the result from an experimentally-determined reference table. The results may be displayed on LEDs or LCDs. There is additionally provided a system to judge whether motion artefact is present by examination of variability of AC signal frequency. If motion is judged to be present, displayed values are frozen and, if this state of affairs continues for any length of time, a warning message is given.

In use, the sensor is closely applied to a well-perfused region of a patient, such as a fingertip. Light from the LEDs needs to pass through a well-perfused region to ensure a good AC signal is obtained. The emergent light pulsates in intensity due to arterial pulsation. Since during systole the internal vessels are dilated, the total path length for the light is increased and intensity falls. Arterial blood is examined exclusively since it alone is the cause of the AC signals.

Patient movement interferes with the operation of pulse oximeters in several ways. If either the LEDs or photodetector is not fixed directly in contact with the skin, their distance from it may vary slightly when the patient moves. By simple $1/d^2$ function through air, measured light levels may change disastrously in real-life situations.

Additionally, even if the optical components are ideally fixed to the skin, the path length between them may change if the tissue is slightly deformed by the movement. Again, light level changes by this mechanism may seriously interfere with measurements. In this case, the function of intensity versus distance is more complicated than $1d/^2$, since, as tissue is deformed, its optical characteristics change. This is because of the mobility of the blood, the major absorbing species at the wavelengths in use; for instance, as the fingertip is compressed, the path length between the optical components will reduce, but, additionally, venous and capillary blood is squeezed out of the light path.

Furthermore, during severe motion, one or both optical transducers may be pulled laterally along the tissue under measurement, effectively changing the measurement site. This typically occurs when the cable connecting the sensor to the instrument is pulled and may cause major optical disturbance.

Since the AC signal is typically only 2-5% of the amplitude of the DC signal, it is this which is proportionally most seriously affected by movement artefact. Considering this, it is a reasonable approximation to apply a filtering algorithm to the AC signals and to ignore errors in the DC signals.

Surprisingly, it has now been discovered that the wanted AC signals, otherwise known as plethysmograph waveforms, have typical frequency versus power spectra as illustrated in accompanying FIG. 1. That is, about 90% of their energy is contained at the fundamental frequency (the pulse rate) with relatively little harmonic energy. Additionally, the unwanted signal caused by motion artefact frequently lies outside the frequency band of the pulse rate. Accompanying FIGS. 2 and 3 illustrate the frequency versus power spectra of signals with which motion artefacts, random and periodic, respectively, are interfering. It follows from these realisations that a bandpass filter may be adapted selectively to exclude motion artefact from wanted signals. Accompanying FIG. 4 illustrates the effectiveness of the present system in the removal of unwanted motion artefact signals from wanted plethysmograph signals.

SUMMARY OF THE INVENTION

In a first embodiment, the present invention relates to a pulse oximeter apparatus characterised in that it comprises a bandpass filter adapted selectively to exclude motion artefact from wanted signal.

In order to achieve this, the filter must initially be tuned to the pulse rate. Moreover, as the pulse rate changes, the filter is so-adapted that its pass-band will follow the frequency change.

DESCRIPTION OF THE PREFERRED EMBODIMENT OF THE INVENTION

As mentioned above, a motion artefact detector system decides by examination of the variability of the amplitude and frequency of the incoming AC signals whether motion artefact is present. If artefact is not judged present, the bandpass filter is tuned to the pulse rate as determined by the normal oximeter algorithms. Additionaly, the AGC system adjusts the input signal levels to the bandpass filter such that there is a large overload margin, for example x16, above the incoming wanted AC signals. When artefact is present, the AGC system is frozen, fixing the gain level, and the bandpass filter is configured in a feedback loop as illustrated in accompanying FIG. 5. The output of the bandpass filters is substantially sinusoidal and so a simple frequency detector, for example a zero crossing counter, is suitable to determine its output frequency. The output of this frequency detector passes through a low-pass loop filter, whose output in turn directly turns the bandpass filter. The system thus formed is a frequency-locked loop or tracking filter.

Thus, when motion artefact is present, the bandpass filters can stay tuned to the pulse rate, tracking its change. The filters selectively exclude motion artefact during operation and the amplitude of the AC signals emergent from the filters may be used by the oximeter as normal. The errors in oxygen saturation measurements, as well as pulse rate, caused by patient movement are thus advantageously reduced.

Figure 6:
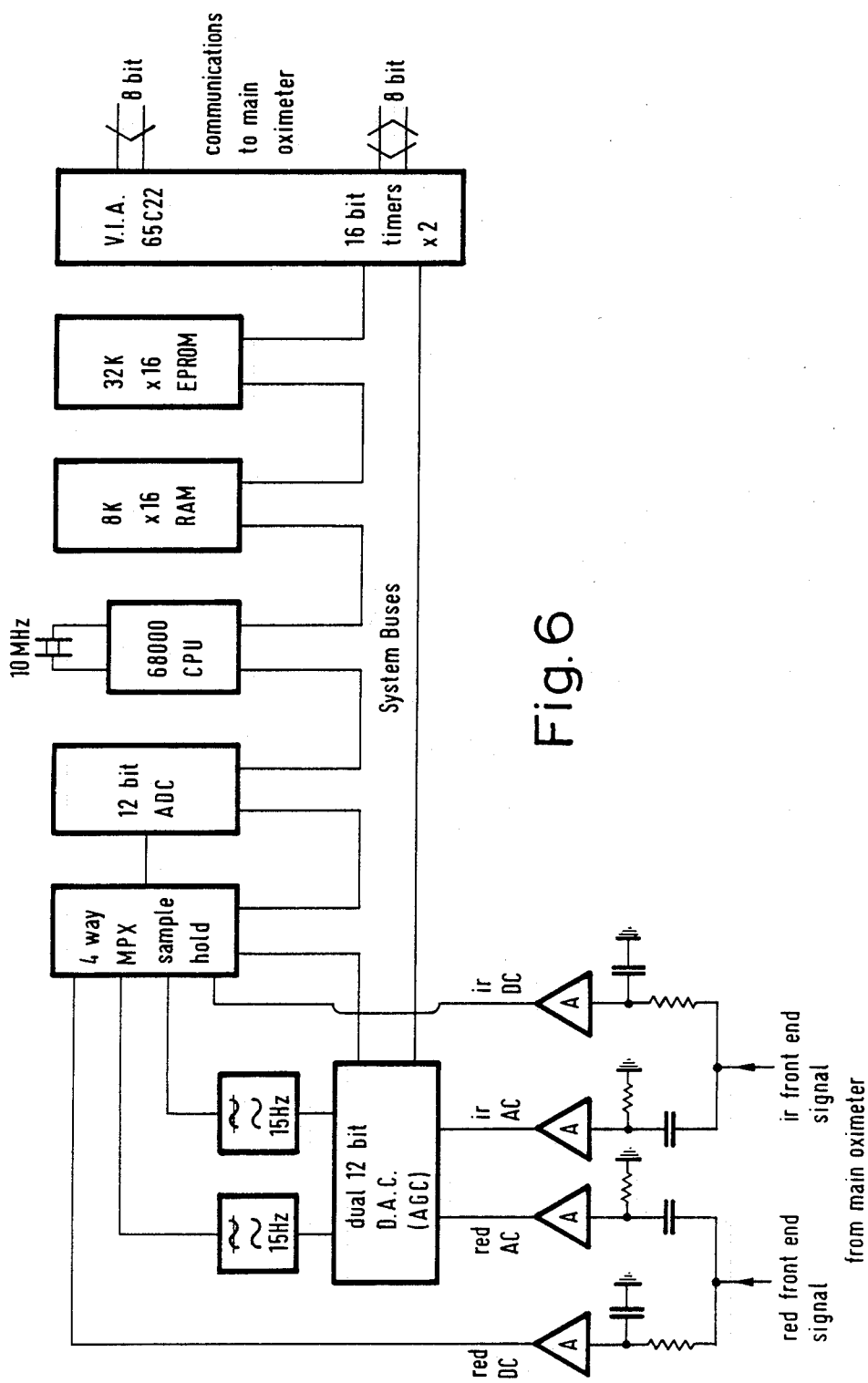
FIG. 6 is a schematic block diagram view of apparatus comprising an environment for the preferred embodiment of the invention.

For purposes of exemplification, the present system has been incorporated into a Novametrix oximeter model 500 as an additional 68000-10 slave processor. A hardware block diagram is illustrated in accompanying FIG. 6.

Figure 1:
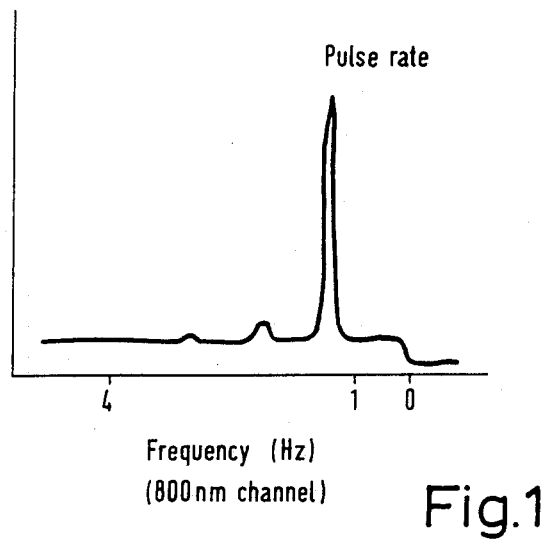
FIG. 1 is a graphical view of the plethysmographic signals found in the environment of the preferred embodiment of the invention.
Figure 2:
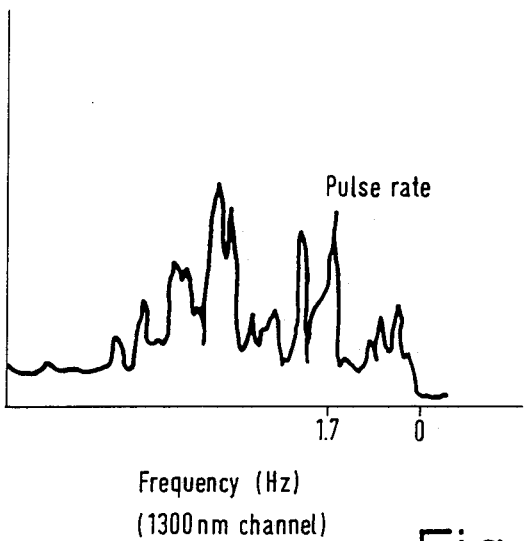
FIG. 2 is a graphical view of the plethysmographic signals with random motion artefacts found in the environment of the preferred embodiment of the invention.
Figure 3:
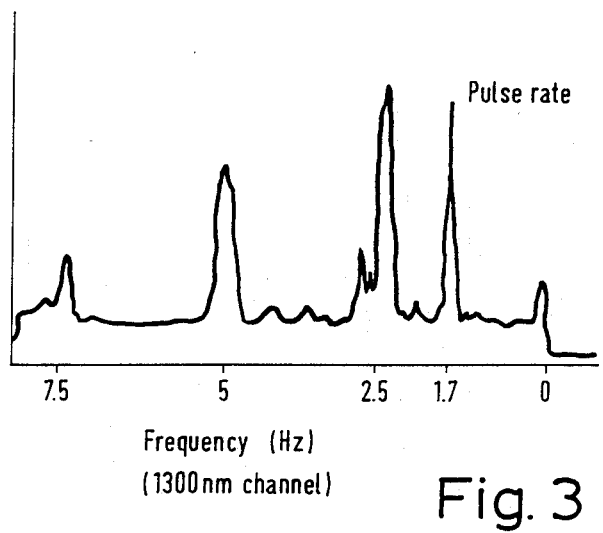
FIG. 3 is a graphical view of the plethysmographic signals with periodic motion artefacts found in the environment of the preferred embodiment of the invention.
Figure 4:
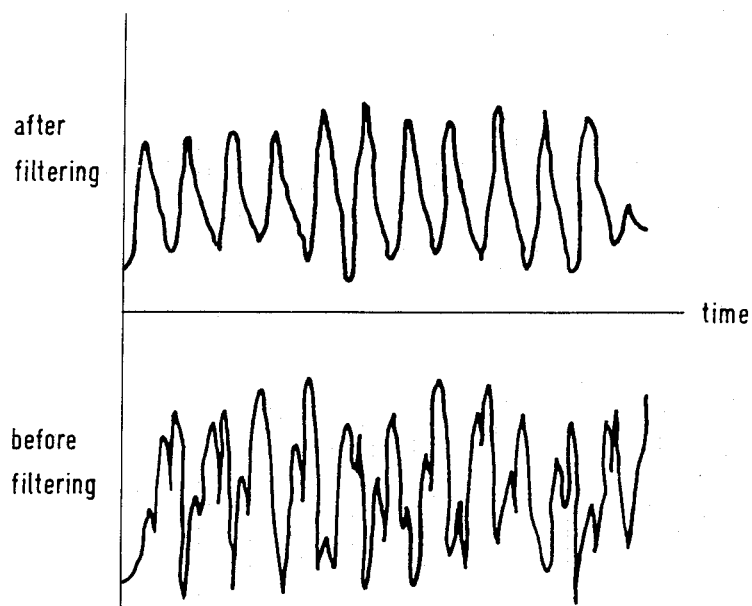
FIG. 4 is a graphical view of plethylsmographic signals demonstrating the effectiveness of the preferred embodiment of the invention.
Figure 5:
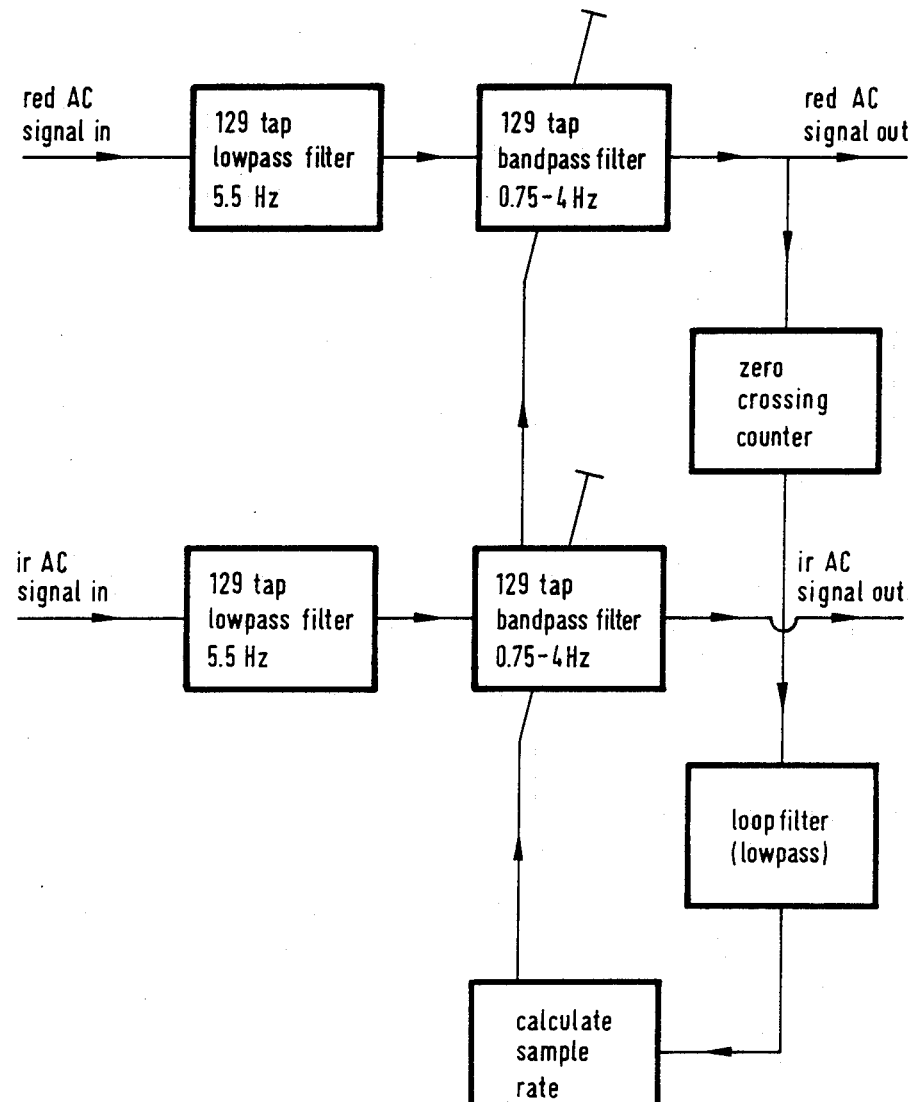
FIG. 5 is a schematic block diagram view of the preferred embodiment of the invention.

Regarding digital signal processing algorithms, the present system is illustrated in accompanying FIG. 5. AC signals are first passed through a high grade 5.5 Hz lowpass filter, 129 tap FIR filter, which is a necessary anti-aliasing filter at the lowest bandpass filter sampling rates. The lowpass filter sampling rate is fixed at 100 Hz. The bandpass filter has fixed coefficients, and is tuned by varying its sample rate as illustrated in accompanying FIG. 5. Finite impulse response (FIR) filters have been used for their predictable frequency versus delay characteristics. The design of this filter is the result of a number of conflicting requirements which are outlined below:

(i) optimal artefact filtering demands a narrow passband and high stop-band rejection, implying long tap-length filters;
(ii) adequate tracking of changes in pulse rate demands a wide pass-band and fast servo loop performance, implying short tap-length filters.

One suitable filter is a 129 tap FIR of sampling rate 15–80 Hz, with −3 dB points ±16% of centre frequency and stopband rejection of −40 dB at ±50% of centre frequency.

I claim:

1. In a pulse oximeter for making a measurement of blood oxygen saturation which produces pulsatile signals in response to a patient's pulsating arterial blood flow in a first variable range of frequencies and motion artefact signals at frequencies outside of said first variable range of frequencies, apparatus for minimizing the effect of said motion artefact signals on said measurement of blood oxygen saturation comprising
   a tunable bandpass filter having an input to which said pulsatile signals and said motion artefact signals are applied;
   a frequency determining means connected to the output of said tunable bandpass filter for determining the frequency of the pulsatile signals at the output of said tunable bandpass filter;
   and a tuning means operatively connected to said frequency determining means and said tunable bandpass filter for tuning said tunable bandpass filter in response to said determined frequency to align the pass band of said band pass filter with the determined frequency of said pulsatile signals whereby motion artefact signals are attenuated.

2. Apparatus according to claim 1 further comprising a first low pass filter connected to the input of said tunable bandpass filter.

3. Apparatus according to claim 1 further comprising a loop filter connected between said frequency determining means and said tuning means.

4. Apparatus according to claim 1 wherein said band pass filter is a digital pass filter tunable by changing its sampling rate, and said tuning means comprises means for changing said sampling rate in accordance with the output of said frequency determining means.

5. Apparatus according to claim 6 wherein said frequency determining means comprises a zero crossing counter.

6. In a pulse oximeter for making a measurement of blood oxygen saturation having a first channel wherein there are produced first pulsatile signals in response to red light absorbed by a patient's pulsating arterial blood flow and a second channel wherein there are produced second pulsatile signals in response to infrared light absorbed by a patient's pulsating arterial blood flow in a first variable range of frequencies, and in which motion artefact signals at frequencies outside of said first variable range of frequencies are produced in said first and second channels, apparatus for minimizing the effect of said motion artefact signals on said measurement of blood oxygen saturation comprising
   a first tunable bandpass filter disposed in said first channel and having an input to which said first pulsatile signals and said first channel motion artefact signals are applied;
   a second tunable bandpass filter disposed in said second channel and having an input to which said second pulsatile signals and said second channel motion artefact signals are applied;
   a frequency determining means connected to the output of at least one of said first and second tunable bandpass filters for determining the frequency of the pulsatile signals at the output of said at least one tunable bandpass filter;
   and a tuning means operatively connected to said frequency determining means and said first and second tunable bandpass filters for tuning said tunable bandpass filters to align the pass bands of the band pass filters with the determined frequency.

* * * * *

UNITED STATES PATENT OFFICE
CERTIFICATE OF CORRECTION

PATENT NO. : 4,955,379

DATED : Sep. 11, 1990

INVENTOR(S) : Peter R. Hall

It is certified that error appears in the above-identified patent and that said Letters Patent is hereby corrected as shown below:

At column 1, line 11, change "$1d/^2$" to --$1/d^2$--.

At column 4, line 30, after "digital" insert --band--.

Signed and Sealed this

Eleventh Day of February, 1992

Attest:

HARRY F. MANBECK, JR.

*Attesting Officer*      *Commissioner of Patents and Trademarks*